United States Patent
Lee et al.

(10) Patent No.: US 12,159,704 B2
(45) Date of Patent: Dec. 3, 2024

(54) METHOD AND APPARATUS FOR PROVIDING COUNSELING SERVICE

(71) Applicant: KAKAO CORP., Jeju-si (KR)

(72) Inventors: Ho Jun Lee, Seongnam-si (KR); Han Yong Park, Seongnam-si (KR); Jung Han Choi, Seongnam-si (KR); Sung Yong Chang, Seongnam-si (KR); Sang Hyeon Seo, Seongnam-si (KR); Hye Ryeon Lee, Seongnam-si (KR)

(73) Assignee: KAKAO CORP., Jeju-Si (KR)

( * ) Notice: Subject to any disclaimer, the term of this patent is extended or adjusted under 35 U.S.C. 154(b) by 112 days.

(21) Appl. No.: 17/886,460

(22) Filed: Aug. 12, 2022

(65) Prior Publication Data
US 2023/0050456 A1     Feb. 16, 2023

(30) Foreign Application Priority Data

Aug. 12, 2021    (KR) .......................... 10-2021-0106423

(51) Int. Cl.
*G16H 20/70* (2018.01)
*H04L 51/02* (2022.01)
*H04L 51/046* (2022.01)

(52) U.S. Cl.
CPC ............. *G16H 20/70* (2018.01); *H04L 51/02* (2013.01); *H04L 51/046* (2013.01)

(58) Field of Classification Search
CPC ........ G16H 20/70; H04L 51/02; H04L 51/046
See application file for complete search history.

(56) References Cited

U.S. PATENT DOCUMENTS

| | | | | |
|---|---|---|---|---|
| 7,636,751 | B2* | 12/2009 | Weaver ............... | H04L 12/1822 709/204 |
| 8,856,236 | B2* | 10/2014 | Moore .............. | H04M 3/42127 704/260 |
| 8,874,672 | B2* | 10/2014 | Ben-Yoseph .......... | H04L 67/75 715/753 |
| 9,760,566 | B2* | 9/2017 | Heck ....................... | G06F 40/30 |
| 9,990,471 | B2* | 6/2018 | Prakash ............. | G06Q 30/0601 |

(Continued)

FOREIGN PATENT DOCUMENTS

| KR | 10-2019-0104119 A | 9/2019 |
|---|---|---|
| KR | 10-2019-0114326 A | 10/2019 |
| KR | 10-2020-0083419 A | 7/2020 |

OTHER PUBLICATIONS

Oct. 30, 2023—(KR) Office Action—App 10-2021-0106423—w/ English machine translation.

(Continued)

*Primary Examiner* — Michael I Ezewoko
(74) *Attorney, Agent, or Firm* — Banner & Witcoff, Ltd.

(57) ABSTRACT

Provided are a method and apparatus for providing a counseling service. A method of operating a counseling center server interworking with an instant messaging service includes activating a connection with a chatbot server linked to a channel in a chat room, calling a chatbot block corresponding to a specific task included in the chatbot server through the chat room, transmitting a message received from a terminal of a user connected to the chat room to the chatbot server as an input of the chatbot block, and transmitting an output of the chatbot block in response to the message received from the chatbot server to the terminal of the user.

20 Claims, 9 Drawing Sheets

(56) References Cited

U.S. PATENT DOCUMENTS

| | | | |
|---|---|---|---|
| 10,574,597 B2* | 2/2020 | Johnson, Jr. | G10L 15/26 |
| 10,574,824 B2* | 2/2020 | Kannan | H04M 3/5166 |
| 10,834,026 B2* | 11/2020 | Nagaraja | G16H 80/00 |
| 10,963,972 B1* | 3/2021 | Gambale | H04N 7/15 |
| 10,964,433 B2* | 3/2021 | Kozloski | G16H 20/40 |
| 10,992,604 B1* | 4/2021 | Knas | H04L 51/04 |
| 11,000,669 B2* | 5/2021 | Derungs | A61B 5/0205 |
| 11,018,998 B1* | 5/2021 | Knas | G06F 40/58 |
| 11,049,605 B1* | 6/2021 | Peters | G16H 20/70 |
| 11,080,777 B2* | 8/2021 | Isaacson | G07F 9/006 |
| 11,128,579 B2* | 9/2021 | Magliozzi | G06F 40/30 |
| 11,177,039 B2* | 11/2021 | Kozloski | G16H 10/60 |
| 11,196,685 B2* | 12/2021 | Blokhin | H04L 51/02 |
| 11,233,756 B2* | 1/2022 | Wu | H04L 51/046 |
| 11,240,181 B1* | 2/2022 | Nagaraja | G16H 40/20 |
| 11,309,086 B1* | 4/2022 | Valliani | G16H 40/63 |
| 11,355,228 B2* | 6/2022 | Appelbaum | G16H 80/00 |
| 11,361,389 B1* | 6/2022 | Gambale | G06N 5/04 |
| 11,431,660 B1* | 8/2022 | Leeds | G10L 15/22 |
| 11,475,069 B2* | 10/2022 | Cui | G06F 40/35 |
| 11,551,804 B2* | 1/2023 | Wu | G16H 80/00 |
| 11,682,493 B2* | 6/2023 | Kozloski | G16H 50/20 705/2 |
| 11,704,501 B2* | 7/2023 | Wu | G06V 20/70 382/156 |
| 11,715,554 B1* | 8/2023 | Aggarwal | G16H 10/20 704/9 |
| 11,744,496 B2* | 9/2023 | Kim | A61B 5/7267 600/300 |
| 11,769,585 B2* | 9/2023 | Youngblood | G16H 20/60 705/3 |
| 11,775,774 B2* | 10/2023 | Darcy | G06F 40/289 704/9 |
| 2003/0131064 A1* | 7/2003 | Bell, III | H04L 51/226 709/206 |
| 2006/0026256 A1* | 2/2006 | Diddee | H04L 51/04 709/207 |
| 2010/0011072 A1* | 1/2010 | Mishchenko | G06Q 10/10 709/206 |
| 2010/0250692 A1* | 9/2010 | Kaminsky | H04L 51/04 709/206 |
| 2012/0030295 A1* | 2/2012 | Bernstein | H04L 51/42 709/206 |
| 2014/0006970 A1* | 1/2014 | Casey | G06Q 50/01 715/753 |
| 2014/0278513 A1* | 9/2014 | Prakash | G06Q 30/0601 705/2 |
| 2017/0295210 A1* | 10/2017 | Choi | H04L 65/1069 |
| 2018/0131645 A1* | 5/2018 | Magliozzi | H04L 51/02 |
| 2018/0145935 A1* | 5/2018 | Blokhin | H04L 51/02 |
| 2018/0315499 A1* | 11/2018 | Appelbaum | G16H 20/60 |
| 2019/0074080 A1* | 3/2019 | Appelbaum | G16H 80/00 |
| 2019/0297033 A1* | 9/2019 | Harma | G06N 3/084 |
| 2019/0324600 A1* | 10/2019 | Wipperf?rth | G06F 3/0482 |
| 2019/0362844 A1* | 11/2019 | Kozloski | G06N 5/022 |
| 2019/0362849 A1* | 11/2019 | Kozloski | G06N 20/00 |
| 2019/0374741 A1* | 12/2019 | Derungs | G06F 3/165 |
| 2020/0082928 A1* | 3/2020 | Wu | G16H 70/20 |
| 2020/0142545 A1* | 5/2020 | Wald | G06N 20/00 |
| 2020/0227160 A1* | 7/2020 | Youngblood | G16H 40/20 |
| 2020/0244605 A1* | 7/2020 | Nagaraja | H04L 51/02 |
| 2020/0251198 A1* | 8/2020 | Lavender | G06N 5/01 |
| 2020/0328907 A1* | 10/2020 | Kim | H04L 41/5093 |
| 2020/0403815 A1* | 12/2020 | Kim | G06F 9/54 |
| 2020/0403949 A1* | 12/2020 | Kim | H04L 51/046 |
| 2021/0098110 A1* | 4/2021 | Periyasamy | G16H 20/70 |
| 2021/0118323 A1* | 4/2021 | Quy | G16H 40/67 |
| 2021/0118547 A1* | 4/2021 | Morris | G16H 50/70 |
| 2021/0118567 A1* | 4/2021 | Kozloski | G16H 20/70 |
| 2021/0287771 A1* | 9/2021 | Lavender | G06N 20/00 |
| 2021/0313041 A1* | 10/2021 | Keene | G16H 40/67 |
| 2022/0006761 A1* | 1/2022 | Magliozzi | H04L 51/066 |
| 2022/0037030 A1* | 2/2022 | Kozloski | G06N 20/00 |
| 2022/0051582 A1* | 2/2022 | Sy | G09B 19/00 |
| 2022/0068451 A1* | 3/2022 | Lavender | G06N 5/04 |
| 2022/0068462 A1* | 3/2022 | Dolan | G10L 25/63 |
| 2022/0068463 A1* | 3/2022 | Dolan | G06Q 50/01 |
| 2022/0105308 A1* | 4/2022 | Youngblood | G16H 15/00 |
| 2022/0115115 A1* | 4/2022 | Paredes Castro | G16H 10/20 |
| 2022/0168539 A1* | 6/2022 | Youngblood | A61M 21/02 |
| 2022/0180067 A1* | 6/2022 | Darcy | G16H 50/30 |
| 2022/0200934 A1* | 6/2022 | Dutta | G06N 3/047 |
| 2022/0310246 A1* | 9/2022 | Larsen | G16H 10/20 |
| 2022/0319669 A1* | 10/2022 | Greenbaum | G16H 20/70 |
| 2022/0375619 A1* | 11/2022 | Appelbaum | G16H 10/60 |
| 2022/0386559 A1* | 12/2022 | Keene | G16H 80/00 |
| 2023/0026871 A1* | 1/2023 | Darcy | A61B 5/7275 |
| 2023/0070179 A1* | 3/2023 | Day | A61B 5/7264 |
| 2023/0070665 A1* | 3/2023 | Day | A61B 5/7264 |
| 2023/0075408 A1* | 3/2023 | Valliani | G06Q 30/0201 |
| 2023/0081359 A1* | 3/2023 | Mirtaheri | G16H 40/67 600/300 |
| 2023/0109946 A1* | 4/2023 | Minkel | G16H 20/00 705/2 |
| 2023/0111078 A1* | 4/2023 | Minkel | G16H 20/10 705/2 |
| 2023/0112522 A1* | 4/2023 | Minkel | G16H 20/00 705/2 |
| 2023/0112908 A1* | 4/2023 | Minkel | G16H 20/00 705/2 |
| 2023/0187031 A1* | 6/2023 | White | G10L 15/22 705/2 |
| 2023/0215543 A1* | 7/2023 | Darcy | G16H 50/70 |
| 2023/0215544 A1* | 7/2023 | Darcy | G16H 80/00 705/2 |
| 2023/0223133 A1* | 7/2023 | Aggarwal | G06F 40/35 704/9 |
| 2023/0225653 A1* | 7/2023 | Kim | A61B 5/6898 600/300 |
| 2023/0260414 A1* | 8/2023 | Lee | G09B 5/02 |
| 2023/0268043 A1* | 8/2023 | Suzuki | G16H 50/20 705/3 |
| 2023/0285711 A1* | 9/2023 | Garcia I Tormo | G16H 20/70 |
| 2023/0394246 A1* | 12/2023 | Darcy | A61B 5/7275 |

OTHER PUBLICATIONS

Apr. 28, 2023—(KR) Korean Office Action—App. No. 10-2021-0106423.

* cited by examiner

METHOD AND APPARATUS FOR PROVIDING COUNSELING SERVICE

CROSS-REFERENCE TO RELATED APPLICATION

This application claims the benefit of Korean Patent Application No. 10-2021-0106423—filed on Aug. 12, 2021, in the Korean Intellectual Property Office, the entire disclosure of which is incorporated herein by reference for all purposes.

BACKGROUND

1. Field of the Invention

One or more example embodiments relate to a method and apparatus for providing a counseling service.

2. Description of the Related Art

Recently, with development of mobile smart devices, the use of online platform services for interaction with other users through networks is increasing. Typical examples of the online platform services for interaction with other users include a social networking service (SNS), which is an online platform that creates and strengthens social relationships through communication, information sharing, and social network expansion among users, and an instant messaging service (IMS), which is an online platform for real-time content communication among two or more users. As the interaction among users through such mobile devices increases, the online platform service supports not only a chat service for daily conversation with other users, but also a function of providing various services based on communication among a plurality of users.

Contact center as a service (CCaaS), a cloud-based service-type contact center solution, may be a service that provides an online counseling platform with various counseling functions including a chat interface and a chatbot server. There is a need for development of CCaaS technology for companies to efficiently conduct and manage counseling by applying smart technology while consumers may request non-face-to-face counseling using mobile devices in an easy and quick way.

SUMMARY

According to an aspect, there is provided a method of operating a counseling center server interworking with an instant messaging service including activating, based on a request to execute a chatbot mode while manned counseling is being conducted through a chat room of a channel registered in the service, a connection with a chatbot server linked to the channel in the chat room, calling a chatbot block corresponding to a specific task included in the chatbot server through the chat room, transmitting, based on the execution of the chatbot mode, a message received from a terminal of a user connected to the chat room to the chatbot server as an input of the chatbot block, and transmitting, based on the execution of the chatbot mode, an output of the chatbot block in response to the message received from the chatbot server to the terminal of the user.

The calling of the chatbot block may include calling the chatbot block corresponding to the specific task based on a call command input from a terminal of a counselor connected to the chat room.

The calling of the chatbot block may include acquiring, based on a search request for a message transmitted through the chat room, a search result from the chatbot server, and calling the chatbot block based on the search result acquired from the chatbot server.

The calling of the chatbot block may include calling the chatbot block corresponding to the specific task based on a call message input from the terminal of the user.

The call message may include a command defined in the chatbot server to call the chatbot block corresponding to the specific task.

The method may further include terminating the execution of the chatbot mode based on at least one of a termination condition of the task and an input for requesting termination of the execution of the chatbot mode, and inactivating the connection with the chatbot server in the chat room based on termination of execution of the chatbot mode.

The method may further include storing, based on the called chatbot block, a message transmitted and received between the terminal of the user connected to the chat room and the chatbot server in a counseling ticket corresponding to the manned counseling.

The method may further include transmitting, based on the execution of the chatbot mode, a message received from a terminal of a counselor to the terminal of the user.

The message received from the terminal of the counselor may be distinguished from the message received from the terminal of the user transmitted to the chatbot server as the input of the chatbot block.

The activating of the connection with the chatbot server may further include transmitting, based on the execution of the chatbot mode, a message for notifying the execution of the chatbot mode through the chat room.

The activating of the connection with the chatbot server may include executing, based on a request to execute the chatbot mode received from a terminal of a counselor, the chatbot mode by activating the connection with the chatbot server linked to the channel in the chat room.

According to another aspect, there is provided a method of operation a counseling center server interworking with an instant messaging service including activating, based on a request to execute a chatbot mode while manned counseling is being conducted through a chat room of a channel registered in the service, a connection with a chatbot server linked to the channel in the chat room, calling a chatbot block corresponding to a specific task included in the chatbot server through the chat room, receiving, based on the execution of the chatbot mode, a message transmitted to the chatbot server through an instant messaging server from a terminal of a user connected to the chat room, and receiving, based on the execution of the chatbot mode, a message transmitted from the chatbot server to the terminal of the user.

The calling of the chatbot block may include calling the chatbot block corresponding to the specific task based on a call command input from a terminal of a counselor connected to the chat room.

The calling of the chatbot block may include acquiring, based on a search request for a message transmitted through the chat room, a search result from the chatbot server, and calling the chatbot block based on the search result acquired from the chatbot server.

The calling of the chatbot block may include calling the chatbot block corresponding to the specific task based on a call message input from the terminal of the user.

The call message may include a command defined in the chatbot server to call the chatbot block corresponding to the specific task.

The method may further include terminating the execution of the chatbot mode based on at least one of a termination condition of the task and an input for requesting termination of the execution of the chatbot mode, and inactivating the connection with the chatbot server in the chat room based on the termination of the execution of the chatbot mode.

The method may further include storing a message transmitted and received between the terminal of the user connected to the chat room and the chatbot server, which is received from the chatbot server, in a counseling ticket corresponding to the manned counseling. According to another aspect, there is provided a counseling center server interworking with an instant messaging service including at least one processor configured to activate, based on a request to execute a chatbot mode while manned counseling is being conducted through a chat room of a channel registered in the service, a connection with a chatbot server linked to the channel in the chat room, call a chatbot block corresponding to a specific task included in the chatbot server through the chat room, transmit, based on the execution of the chatbot mode, a message received from a terminal of a user connected to the chat room to the chatbot server as an input of the chatbot block, and transmit, based on the execution of the chatbot mode, an output of the chatbot block in response to the message received from the chatbot server to the terminal of the user.

According to another aspect, there is provided a counseling center server interworking with an instant messaging service including at least one processor configured to activate, based on a request to execute a chatbot mode while manned counseling is being conducted through a chat room of a channel registered in the service, a connection with a chatbot server linked to the channel in the chat room, call a chatbot block corresponding to a specific task included in the chatbot server through the chat room, receive, based on the execution of the chatbot mode, a message transmitted to the chatbot server through an instant messaging server from a terminal of a user connected to the chat room, and receive, based on the execution of the chatbot mode, a message transmitted from the chatbot server to the terminal of the user Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
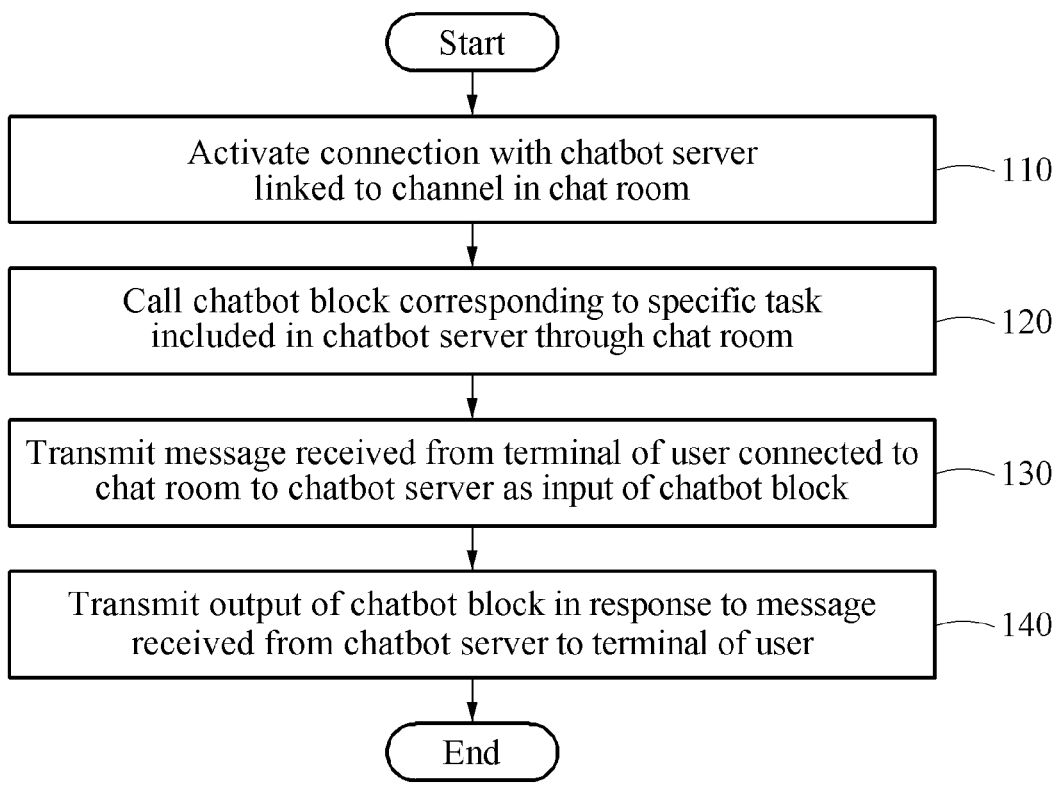
FIG. 1 is an operation flowchart illustrating a method of operating a counseling center server according to an example embodiment.

Although terms of "first," "second," and the like are used to explain various components, the components are not limited to such terms. These terms are used only to distinguish one component from another component. For example, a first component may be referred to as a second component, or similarly, the second component may be referred to as the first component within the scope of the present disclosure.

When it is mentioned that one component is "connected" or "accessed" to another component, it may be understood that the one component is directly connected or accessed to another component or that still other component is interposed between the two components.

As used herein, the singular forms "a," "an," and "the" are intended to include the plural forms as well, unless the context clearly indicates otherwise. It will be further understood that the terms "comprise" and/or "have," when used in this specification, specify the presence of stated features, integers, steps, operations, elements, components or a combination thereof, but do not preclude the presence or addition of one or more other features, integers, steps, operations, elements, components, and/or groups thereof.

Hereinafter, example embodiments will be described in detail with reference to the accompanying drawings. When describing the example embodiments with reference to the accompanying drawings, like reference numerals refer to like components and a repeated description related thereto will be omitted.

FIG. 1 is an operation flowchart of a method of operating a counseling center server according to an example embodiment.

Referring to FIG. 1, a method of operating a counseling center server interworking with an instant messaging service includes activating a connection with a chatbot server linked to a channel in a chat room 110, calling a chatbot block corresponding to a specific task included in the chatbot server through the chat room 120, transmitting a message received from a terminal of a user connected to the chat room to the chatbot server as an input of the chatbot block 130, and transmitting an output of the chatbot block in response to the message received from the chatbot server to the terminal of the user 140.

The counseling center server according to an example embodiment may correspond to a server that provides a counseling service by interworking with an instant messaging service. The counseling service refers to a counseling service that uses an instant messenger connected to an instant messaging server that provides an instant messaging service as a counseling medium, and a user may use the counseling service by subscribing to the instant messaging service or through a registered account. The counseling center server and the instant messaging server may be included in a counseling system for providing the counseling service, and a detailed configuration of the counseling system will be described in detail below.

The instant messaging server according to an example embodiment may provide various types of accounts, such as a personal account, a corporate account, or a service account, to use the instant messaging service. The personal account may be an account for general users, the corporate account may be an account for specific companies, and the service account may be an account for specific services. The corporate account or the service account may be referred to as a channel.

The counseling service according to an example embodiment may be provided in a form of counseling through a channel registered in the instant messaging service. Counseling through a channel may refer to the counseling conducted in a chatting manner between a channel and an account requesting the counseling for the channel. For example, the counseling service may be provided in a chatting manner using an instant messenger between a personal account (an account of a natural individual) registered in the instant messaging service of a first user corresponding to a general user and a channel registered in the instant messaging service of a second user corresponding to a specific company or a specific service provider. Hereinafter, the 'counseling center server' may be briefly referred to as a 'server'.

Operation 110 according to an example embodiment may include activating a connection with a chatbot server linked to a channel in the chat room based on a request to execute a chatbot mode while manned counseling is being conducted through a chat room of a channel registered in the instant messaging service. The channel may correspond to a corporate account or a service account of the second user. The chat room of the channel may be created based on a request of the first user for counseling on the channel. The first user may correspond to a user having a personal account, a corporate account, or a service account registered in the instant messaging service.

According to an example embodiment, the first user may request the server for the counseling through the channel of the second user using a terminal. Hereinafter, the terminal logged in with an account of the first user may be referred to as the terminal of the first user. For example, the terminal of the first user may receive a command of the first user for requesting the counseling from a website or application linked to the channel of the second user, and transmit a signal for requesting the counseling through the channel of the second user to the server. As another example, the terminal of the first user may respond to an input of the first user selecting (e.g., click) a button for requesting the counseling on an interface related to the channel of the second user provided in the instant messenger connected to the instant messaging server so as to transmit a signal for requesting the counseling through the channel of the second user to the server. In this case, the request for the counseling on the channel of the second user may be transmitted to the counseling center server through the instant messaging server.

According to an example embodiment, the first user may request the instant messaging server for the counseling through the channel of the second user using the terminal. For example, the terminal of the first user may receive a command of the first user for requesting the counseling from a website or application linked to the channel of the second user to transmit a signal for requesting the counseling through the channel of the second user to the instant messaging server. As another example, the terminal of the first user may respond to the input of the first user selecting (e.g., click) a button for requesting the counseling on the interface related to the channel of the second user provided in the instant messenger connected to the instant messaging server so as to transmit a signal for requesting the counseling through the channel of the second user to the instant messaging server.

The instant messaging server according to an example embodiment may create, in response to an input for requesting the counseling on the channel of the second user, a chat room for the counseling on the channel of the second user. The chat room for the counseling of a channel may correspond to a virtual chat space for transmitting and receiving a chat message between a user account requesting the counseling on the channel and a channel. An entity conducting the counseling linked to the channel may access a chat room for the counseling of the channel, and transmit and receive chat messages with an account of a user participating in the chat room. For example, the entity conducting the counseling may include a counselor as a natural individual and a chatbot. Hereinafter, a chat room of a channel may be understood to refer to a chat room for the counseling of a channel.

According to an example embodiment, the counseling through the chat room may be conducted as the manned counseling with the counselor as the natural individual. For example, the manned counseling may be conducted as a 1:1 chatting through a chat interface between the account of the first user requesting the counseling and an account of a counselor linked to the channel of the second user, and the account of the counselor linked to the channel of the second user may correspond to an account capable of transmitting and receiving a chat message regarding the counseling with the first user account requesting the counseling using the channel of the second user. According to an example embodiment, the counseling through the chat room may be conducted as unmanned counseling using a chatbot without including the counselor who is the natural individual.

According to an example embodiment, the account of the counselor linked to the channel may correspond to an account granted access to a chat room for counseling of the channel. The right to access the chat room of the channel may correspond to the right to transmit a message through the chat room of the channel using the channel and receive the message transmitted through the chat room of the channel.

According to an example embodiment, the right to access the chat room of the channel of the account of the counselor linked to the channel may be limited to a part of the chat room of the channel. For example, of chat rooms created for counseling of the channel, an account of a first counselor may have the right to access a part allocated to the account of the first counselor, and an account of a second counselor may have the right to access another part allocated to an account of the second counselor.

The channel according to an example embodiment may be linked to the chatbot server. The chatbot server is a server that provides a chatbot service designed to have conversation or conduct counseling with a user. For example, a chatbot service, configured to extract an intent and an entity by parsing an input query and create a response corresponding to the query based on the extracted intent and entity, may be provided.

According to an example embodiment, the chatbot server linked to the channel may be connected to a chat room of the channel. As an example, the server may activate a connection between the chatbot server linked to the channel and the chat room based on a request to execute the chatbot mode while the manned counseling is being conducted through the chat room of the channel. The chatbot mode may correspond to a mode in which the counseling with the chatbot server is conducted during the manned counseling.

Operation 110 according to an example embodiment may include executing, based on a request to execute the chatbot mode received from a terminal of a counselor, the chatbot mode by activating a connection with a chatbot server linked to a channel in a chat room of the channel. In other words, the request to execute the chatbot mode may be received from the terminal of the counselor. For example, when it is determined that the counseling with the chatbot server needs to be conducted during the manned counseling, the counselor may input a signal for requesting execution of the chatbot mode to the server through a chat interface provided to the terminal of the counselor. The chat interface provided to the terminal of the counselor including a function of requesting the execution of the chatbot mode will be described in detail below.

Operation 110 according to an example embodiment may further include transmitting, based on the execution of the chatbot mode, a message for notifying the execution of the chatbot mode through the chat room of the channel. The server may transmit a message for notifying the execution of the chatbot mode through the chat room of the channel in which the execution of the chatbot mode is requested so as to notify the first user connected to the chat room of the channel that the chatbot mode is executed and subsequent counseling is conducted through the chatbot.

Operation 120 according to an example embodiment may include calling a chatbot block corresponding to a specific task included in the chatbot server through the chat room of the channel in which the chatbot mode is executed.

According to an example embodiment, the chatbot server may include a chatbot block implemented to output a response corresponding to an input query. The chatbot block may be defined in a unit of tasks and include expected utterances, actions, and response messages. The chatbot block may correspond to a program module implemented to extract an intent and entity from the input query based on the expected utterance, perform a defined action corresponding to the extracted intent and entity, and output a response message based on the executed action. As an example, the chatbot block may output a response to the input query using various methods according to the general operating principle of the chatbot server, such as rule-based, natural language processing-based, and learning-based, and a combination of various methods. A task refers to a defined function performed through the chatbot, and may include, for example, 'product recommendation', 'purchasable product information', 'progression of refund procedure', and 'change shipping address'. A sequence of a plurality of chatbot blocks may be defined in correspondence to a single task. For example, corresponding to the task of 'change shipping address', a first chatbot block input with a name or order number of a purchaser to check an existing shipping address and a second chatbot block input with a new shipping address to change order details may be defined, and a sequence of a plurality of chatbot blocks may be included based on possible scenarios according to an input of a user.

Operation 120 according to an example embodiment may include calling a chatbot block corresponding to a specific task based on a call command input from a terminal of a counselor connected to the chat room of the channel. The terminal of the counselor may select a chatbot block corresponding to a specific task through the chat interface, and transmit a call command related to the selected chatbot block to the server. The terminal of the counselor may select a chatbot block corresponding to the specific task based on a message received through a chat room of a channel. For example, the terminal of the counselor may transmit a call command of the chatbot block corresponding to the task of changing the shipping address to the server through the chat interface in the chat room of the channel in which the counseling message requesting to change the shipping address is received.

Operation 120 according to an example embodiment may include calling a chatbot block corresponding to a specific task based on a call message input from the terminal of the first user. The call message may include a command defined in the chatbot server to call a chatbot block corresponding to the specific task. For example, the call message may include a text command requesting the chatbot server to execute a chatbot block corresponding to the specific task. The call message may include text in a form to distinguish the message from a general message transmitted to the terminal of the counselor through the chat room. For example, the call message may include text in a form starting with a specific identification symbol, and a text message starting with the specific identification symbol may be recognized as a message transmitted to the chatbot server.

According to an example embodiment, the counselor may transmit a message instructing the first user to input a message including a command for calling the chatbot block through the chat room of the channel in order to call the chatbot block corresponding to the specific task. For example, when the first user requests to change the shipping address through the chat room of the channel, the counselor may transmit, to the first user, a message (e.g., "Please input 'requesting to change shipping address' in the chat window") that guides the user to input a call command (e.g., request to change the shipping address) of the chatbot block corresponding to the task of changing the shipping address through the chat room of the channel.

Operation 120 according to an example embodiment may include acquiring a search result from a chatbot server based on a search request for the message transmitted through a chat room of a channel, and calling a chatbot block based on the search result acquired from the chatbot server. According to an example embodiment, the chatbot server, a search medium used to acquire a search result for a search request, may be used as a means to assist the counselor using the counseling service to conduct the counseling. The counselor connected to the chat room of the channel may request the server to search for a message received through the chat room by using a terminal logged in with an account of the counselor (hereinafter, referred to as a terminal of the counselor).

According to an example embodiment, the server may transmit a search request to the chatbot server, and acquire a search result including information for calling a chatbot block corresponding to the search request from the chatbot server. A search request for a message transmitted to a chat room for counseling on a channel may include a search request for a search word determined by the counselor to respond to a message, a search request for a keyword extracted from the message, and a search request for the entire message. An operation of transmitting the search request to the chatbot server may include an operation of transmitting, to the chatbot server, a command in which a search word corresponding to the search request is changed into a form for requesting a search medium for data. For example, when the search request is based on a specific keyword, the keyword or a value obtained by converting the keyword into a parameter corresponding to the search medium may be transmitted to the chatbot server. Alternatively, when the search request is based on the entire message, the keyword may be extracted from the message and transmitted to the chatbot server, or the entire message may be transmitted.

According to an example embodiment, the chatbot server may identify a task corresponding to the input search request, and may provide information for calling a chatbot block corresponding to the identified task to the server as a search result. The server may call the chatbot block through the chat room in response to an input of the counselor for selecting a search result including information for calling the chatbot block. The information for calling the chatbot block is information required to transmit a command for requesting the execution of the chatbot block to the chatbot server, including, for example, information indicating the chatbot block and the address in which the chatbot block is stored in the chatbot server.

When the chatbot block is called by operation 120 according to an example embodiment, the chatbot server may transmit a message for receiving the query of the chatbot block through the chat room of the channel, and output a result of processing the query input to the chatbot block according to the action defined in the chatbot block. The result of processing the input query according to the action defined in the chatbot block may include a message created in response to the input query and/or an action of calling another chatbot block corresponding to the task to perform the next action of the task. The result that is output from the chatbot server may be transmitted to the terminal of the first user in the form of a message through the chat room of the channel. The result transmitted in the form of a message may include a message corresponding to an answer to the inquiry of the first user, and may include a message for receiving the query of the chatbot block called to perform the next operation of the task.

Figure 2A:
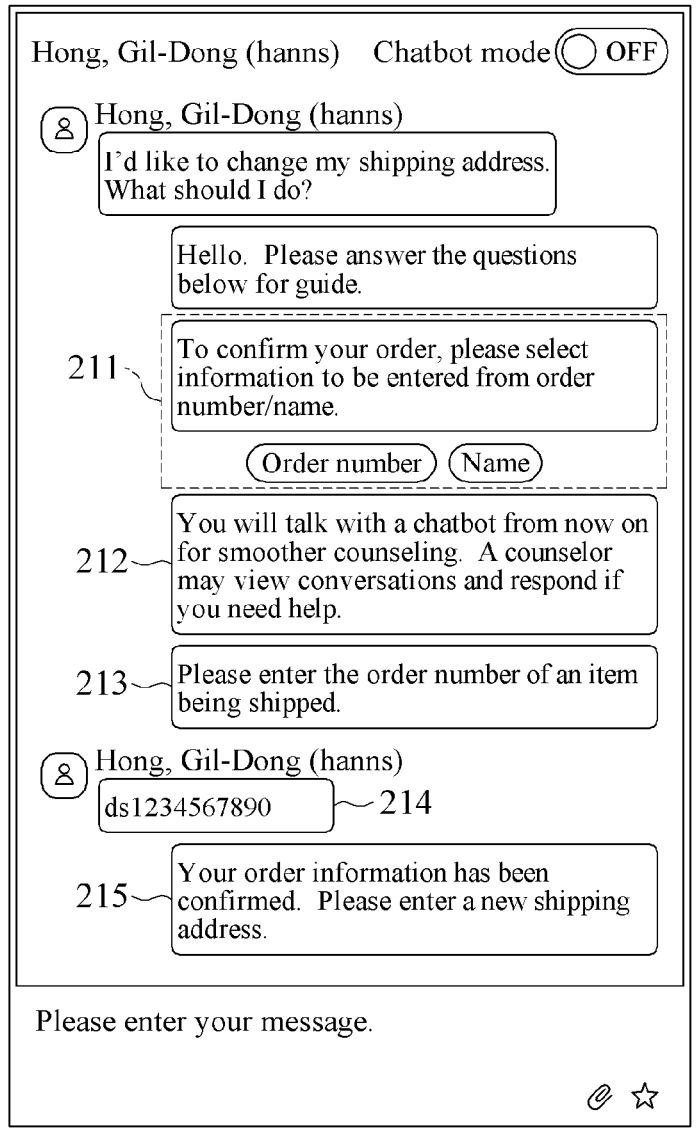
FIGS. 2A and 2B are diagrams illustrating an example of a chat window through which a message for counseling is transmitted and received according to execution of a chatbot mode during manned counseling according to an example embodiment.

For example, referring to FIG. 2A, when the chatbot block corresponding to the task of 'change shipping address' is called by operation 120 according to an example embodiment, the chatbot server may transmit a message 211 for receiving the query of the chatbot block through the chat room of the channel. When an input for selecting 'order number' is received from the terminal of the first user, the input for selecting 'order number' is input as a query of the chatbot block, and the result of processing the input query according to the action defined in the chatbot block may be output as a message 213 requesting the input of the order number through the chat room of the channel. The message 213 requesting the input of the order number may correspond to a message for receiving a query of the chatbot block called to perform the next operation of the task of 'change shipping address'. When the message 214 responding to the order number is received from the terminal of the first user, the message 214 responding to the order number may be input as a query of the chatbot block, and the result of processing the input query according to the action defined in the chatbot block may be output as a message 215 requesting the input of a new shipping address through the chat room of the channel. The message 215 requesting the input of a new shipping address may correspond to a message for receiving a query of the chatbot block called to perform the next operation of the task of 'change shipping address'.

Figure 2B:
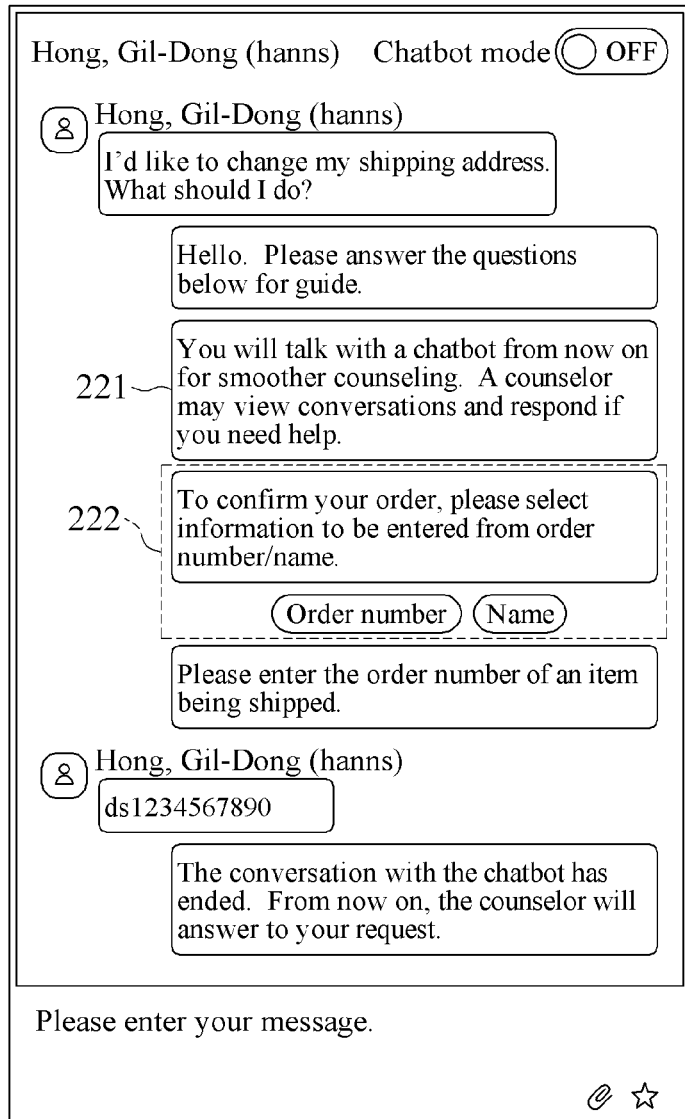

According to an example embodiment, the order of operations 110 and 120 may be changed. For example, referring to FIG. 2A, the server may call a chatbot block, and transmit a message 211 for receiving a query of the chatbot block called through the chat room of the channel. Based on a request to execute the chatbot mode received from the terminal of the counselor after the chatbot block is called through the chat room of the channel, the server may activate the connection with the chatbot server in the chat room. As the connection with the chatbot server is activated, the server may transmit a message 212 for notifying the execution of the chatbot mode through the chat room of the channel. For another example, referring to FIG. 2B, the server may activate the connection with the chatbot server in the chat room based on the request to execute the chatbot mode received from the terminal of the counselor. As the connection with the chatbot server is activated, the server may transmit a message 221 for notifying the execution of the chatbot mode through the chat room of the channel. The server may call the chatbot block after activating the connection with the chatbot server in the chat room based on the request to execute the chatbot mode received from the terminal of the counselor, and transmit a message 222 for receiving the query of the chatbot block called through the chat room.

Operation 130 according to an example embodiment may include transmitting, based on the execution of the chatbot mode, a message received from the terminal of the first user connected to the chat room of the channel to the chatbot server as an input of the chatbot block. Operation 140 according to an example embodiment may include transmitting, based on the execution of the chatbot mode, the output of the chatbot block in response to the message received from the chatbot server to the terminal of the first user. In other words, the message transmitted from the terminal of the first user may be transmitted to the chatbot server through the server, and the message transmitted from the chatbot server may be transmitted to the terminal of the first user through the server.

According to an example embodiment, the message transmitted from the terminal of the first user may be transmitted to the chatbot server through the instant messaging server. By transmitting the message received from the chatbot server to the server, the message of the first user transmitted to the chatbot server may be shared with the server. The message corresponding to the response created in the chatbot server may be transmitted to the terminal of the first user through the instant messaging server. By transmitting the message created in the chatbot server to the server, the message of the chatbot server transmitted to the terminal of the first user may be shared with the server. An operation of a counseling center server that receives a message transmitted and received between a chatbot server and the terminal of the first user through an instant messaging server from the chatbot server will be described in detail with reference to FIG. 4 below.

According to an example embodiment, a message transmitted and received between the chatbot server and the terminal of the first user may be stored in a counseling ticket corresponding to the manned counseling. In other words, the method of operating the counseling center server may further include storing, based on the called chatbot block, the message transmitted and received between the terminal of the first user connected to the chat room of the channel and the chatbot server in the counseling ticket corresponding to the manned counseling.

According to an example embodiment, a message transmitted and received between the chatbot server and the terminal of the first user may be stored in the counseling ticket corresponding to the unmanned counseling. In other words, when the chatbot block is called during the manned counseling with the counselor, the counseling ticket corresponding to the manned counseling is terminated or temporarily suspended, and a counseling ticket corresponding to the unmanned counseling with the chatbot server may be created. The message transmitted and received between the chatbot server and the terminal of the first user may be stored in the counseling ticket corresponding to the created unmanned counseling.

According to an example embodiment, the counseling ticket, a unit of counseling objectified in the server, may correspond to a session for counseling between a specific user and a counselor or chatbot linked to a specific channel. The counseling between the specific user and the specific channel is objectified as the counseling ticket and stored in the server, and the counseling ticket may include a chat log transmitted and received during the counseling between the specific user and the specific channel.

As an example, the counseling ticket may be created in correspondence to the chat room as the first user requesting the counseling inputs a chat message into the chat room of the channel through the chat interface for counseling. When the counseling type at the time of inputting the chat message of the first user corresponds to the unmanned counseling, a type of counseling ticket corresponding to the unmanned counseling may be created. When the counseling type at the time of inputting the chat message of the first user corresponds to the manned counseling, a type of counseling ticket corresponding to the manned counseling may be created.

Figure 3:
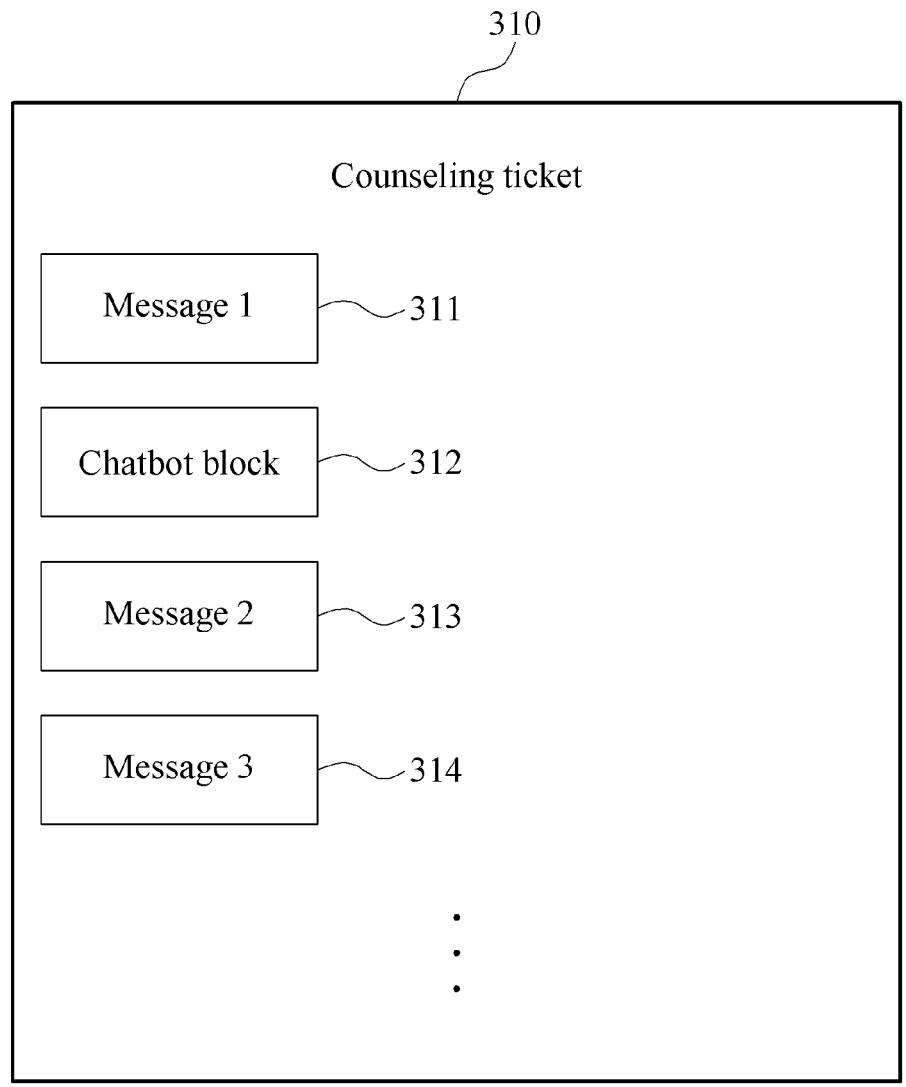
FIG. 3 is a diagram illustrating a counseling ticket according to an example embodiment.

For example, referring to FIG. 3, messages 311, 313, and 314 transmitted and received through the corresponding chat room and the called chatbot block 312 may be stored in the counseling ticket 310 in a chronological order. The chatbot block 312 stored in the counseling ticket may include a message of the first user received in the chatbot server as the query of the chatbot block and a message created in the corresponding chatbot server output by the action defined in the chatbot block in response to the message of the first user.

According to an example embodiment, while the chatbot mode is running, the counselor may transmit a message to the first user through a chat room of a channel. A message transmitted from the terminal of the counselor through the chat room of the channel may be transmitted to the terminal of the first user, but may not be transmitted to the chatbot server. In other words, the method of operating the counseling center server according to an example embodiment may further include transmitting, based on the execution of the chatbot mode, a message received from the terminal of the counselor to the terminal of the first user. The message received from the terminal of the counselor may be distinguished from a message received from the terminal of the first user transmitted to the chatbot server as an input of the chatbot block. The server may distinguish between a message received from the terminal of the first user connected to the chat room of the channel and a message received from the terminal of the counselor, and the message received from the terminal of the counselor is not transmitted to the chatbot server, while the message received from the terminal of the first user may be transmitted to the chatbot server.

According to an example embodiment, the terminal of the counselor may use a search function through a chat interface while the chatbot mode is running. In response to the search request of the counselor while the chatbot mode is running, the search results provided to the terminal of the counselor may not include the search results of the chatbot server, and may include search results of other search media other than the chatbot server. Search media other than the chatbot server may include, for example, a database linked to a channel. In other words, since the response message of the chatbot server is transmitted to the terminal of the first user through the chat room of the channel while the chatbot mode is running, the response of the chatbot server may not be provided as a search result.

According to an example embodiment, in response to the search request from the counselor while the chatbot mode is running, the search result provided to the terminal of the counselor may include the search result of the chatbot server. In other words, the search results provided in response to the search request of the counselor may include the search results of the chatbot server together with the search results of other media.

According to an example embodiment, the method of operating the counseling center server may further include terminating execution of the chatbot mode based on at least one of a termination condition for a task and an input for requesting termination of execution of the chatbot mode, and inactivating, based on the termination of execution of the chatbot mode, the connection with the chatbot server in the chat room of the channel. The termination condition for a task may include, for example as a condition for terminating a response output operation of the chatbot server corresponding to the task defined in the chatbot server, conditions that are satisfied when responses according to the chatbot block corresponding to the task are all output or when the chatbot block corresponding to the task is discontinued. An input for requesting termination of execution of the chatbot mode may be received through a chat interface in the terminal of the counselor or the terminal of the first user.

The server according to an example embodiment may terminate the execution of the chatbot mode when the termination condition for the task is satisfied or when an input for requesting the termination of execution of the chatbot mode is received. When the execution of the chatbot mode is terminated, the connection between the chat room of the channel and the chatbot server may be inactivated, and the message transmitted from the terminal of the first user may be transmitted to the terminal of the counselor without being transmitted to the chatbot server. In other words, when the chatbot mode is terminated, the counseling through the chat room of the channel may be conducted by transmitting and receiving a chat message with the counselor again.

Figure 4:
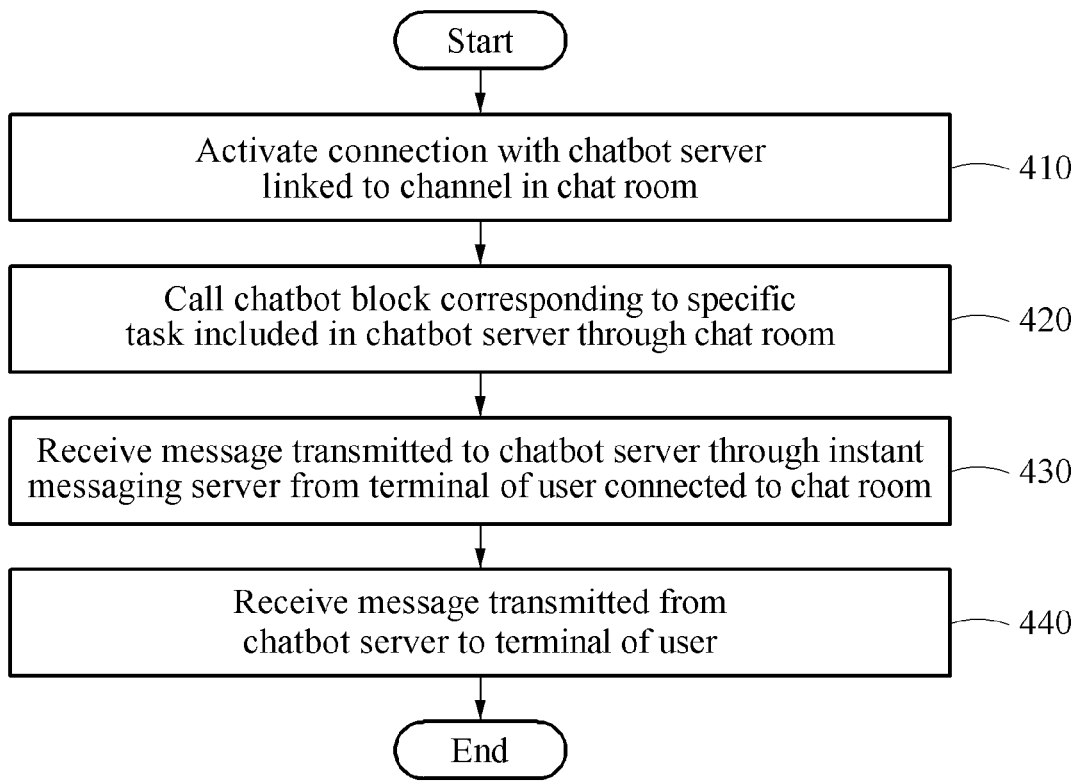
FIG. 4 is an operation flowchart of a method of operating a counseling center server according to an example embodiment.

FIG. 4 is an operation flowchart of a method of operating a counseling center server according to an example embodiment.

Referring to FIG. 4, a method of operating a counseling center server interworking with an instant messaging service may include activating a connection with a chatbot server linked to a channel in a chat room 410, calling a chatbot block corresponding to a specific task included in the chatbot server through the chat room 420, receiving a message transmitted to the chatbot server through the instant messaging server from the terminal of the user connected to the chat room 430, and receiving a message transmitted from the chatbot server to the terminal of the user 440. The channel may correspond to a corporate account or a service account of a second user. The chat room of the channel may be created based on a request of a first user for counseling on the channel. The first user may correspond to a user having a personal account, a corporate account, or a service account registered in the instant messaging service.

Operation 410 according to an example embodiment may include activating a connection with a chatbot server linked to a channel in the chat room based on a request to execute the chatbot mode while the manned counseling is being conducted through a chat room of a channel registered in the instant messaging service. Operation 410 according to an example embodiment may correspond to operation 110 of FIG. 1.

Operation 420 according to an example embodiment may include calling a chatbot block corresponding to a specific task included in the chatbot server through a chat room of a channel. Operation 420 according to an example embodiment may correspond to operation 120 of FIG. 1.

Operations 430 and 440 according to an example embodiment may include, as described above, receiving a message transmitted and received from the chatbot server through the chat room of the channel while a message between the chatbot server and the terminal of the first user is transmitted and received through the instant messaging server.

More specifically, operation 430 according to an example embodiment may include receiving, based on the execution of the chatbot mode, a message transmitted to the chatbot server through the instant messaging server from the terminal of the first user connected to the chat room of the channel. The chatbot server may transmit a message transmitted from the terminal of the first user to the server, and the instant messaging server may transmit a message transmitted from the terminal of the first user to the server.

Operation 440 according to an example embodiment may include receiving, based on the execution of the chatbot mode, a message transmitted from the chatbot server to the terminal of the first user. The chatbot server may transmit the created message to the terminal of the first user through the instant messaging server, and may share the created message with the server.

As described above, the message transmitted and received through the chat room of the channel between the chatbot server and the first user may be stored in the counseling ticket corresponding to the chat room. The server may store, in the counseling ticket, the message that is received from the chatbot server and transmitted and received between the chatbot server and the terminal of the first user. The message transmitted and received between the chatbot server and the first user may be stored in the counseling ticket corresponding to the manned counseling created in correspondence to the chat room before the chatbot block is called in the chat room, or in the counseling ticket corresponding to the unmanned counseling created in correspondence to the chat room by the call of the chatbot block.

Figure 5:
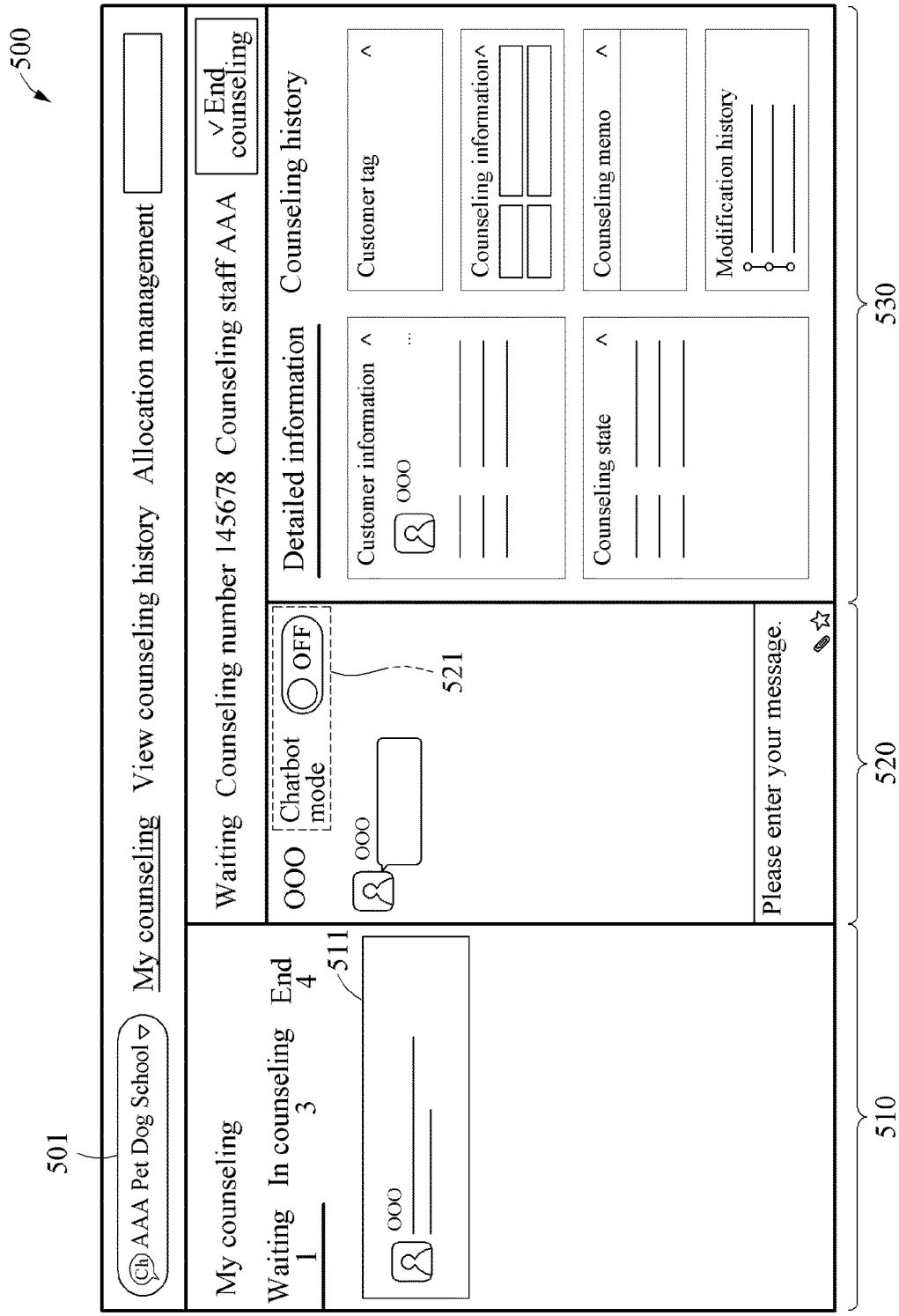
FIG. 5 is a diagram illustrating a screen of an interface related to a counseling center module according to an example embodiment.

FIG. 5 is a diagram illustrating a screen of an interface related to a counseling center module according to an example embodiment.

According to an example embodiment, the counseling center server may create the counseling center module corresponding to the channel in response to a request for opening the counseling center of a channel registered in the instant messaging service, and interwork the chatbot server linked to the channel with the counseling center module. The counseling center module, an instance created in correspondence to a channel in the server, may include data for providing and managing the counseling service for the channel. For example, the counseling center module may include data for providing counseling services such as account(s) of the counselor(s) linked to the corresponding channel, chat room(s) created for the counseling of the channel, counseling history, and counseling performance outcomes. The counseling center module may correspond to an instance having a 1:1 correspondence relation with a channel, and the counseling center module corresponding to a specific channel may not correspond to another channel. The server may create and/or delete the counseling center module according to the request from the channel. A channel in which the counseling center module is created may use a counseling service function provided in the server.

A request to open the counseling center according to an example embodiment is to request to create the counseling center module corresponding to a specific channel registered in the server, and may be received from a terminal logged in with the account of an administrator of the channel or a terminal logged in with the account of a user authorized to manage the counseling center of the channel. Hereinafter, the 'account of an administrator of a channel' or the 'account of a user authorized to manage a counseling center of a channel' is referred to as the 'account of a counseling center administrator'.

According to an example embodiment, when there is a chatbot server linked to a channel in which the counseling center module is created, the server may link the chatbot server with the counseling center module. As described above, the chatbot server may be used as a means to assist the counselor using the counseling service to conduct the counseling.

According to an example embodiment, when the counseling center module corresponding to the channel is created, the account of the counseling center administrator may register the account of the counselor linked to the channel in the counseling center module. An interface related to the counseling center module may be provided to the terminal logged in with the account of the counselor registered in the counseling center module. By accessing the chat room created for the counseling through the interface related to the counseling center module provided in the terminal to transmit and receive messages, the counselor may conduct the counseling with the user account requesting the counseling and use functions related to counseling services, such as uses of a search function to create a message for the counseling.

Referring to FIG. 5, an interface 500 related to the counseling center module corresponding to a specific channel 501 according to an example embodiment may be provided to a terminal logged in with an account of a counselor linked to the channel (hereinafter, referred to as a terminal of the counselor). The interface 500 provided to the terminal of the counselor may include a list 510 of chat rooms allocated to the account of the counselor. By selecting (e.g., click) the interfacing object 511 related to the chat room displayed in the list of chat rooms, the counselor may request connection to the chat room to the server. For example, when the counselor requests connection to the chat room to the server by clicking the interfacing object 511 related to the chat room, the server may respond to the connection request to provide a chat window 520 corresponding to the chat room to the terminal of the counselor. The terminal of the counselor may request, in response to a message input by the counselor in the chat window 520, the server to transmit the message to the account of the user participating in the chat room. The counselor may conduct the counseling with the user by transmitting and receiving messages to and from the account of the user participating in the chat room through the chat window 520.

According to an example embodiment, the chat window 520 may include an interfacing object 521 in which a function of requesting execution and termination of the chatbot mode is implemented. In a state in which the chatbot mode of the chat room corresponding to the chat window 520 is not running, the terminal of the counselor may request the server to execute the chatbot mode in response to an input (e.g., click) of the counselor selecting the interfacing object 521 for requesting execution and termination of the chatbot mode. Alternatively, in a state in which the chatbot mode of the chat room corresponding to the chat window 520 is running, the terminal of the counselor may request the server to terminate the execution of the chatbot mode in response to an input (e.g., click) of the counselor selecting the interfacing object 521 for requesting execution and termination of the chatbot mode.

According to an example embodiment, the chat interface 500 may further include a window 530 for providing information on the counseling in addition to the list 510 of chat rooms and the chat window 520. The information on the counseling may include, for example, information on a user requesting the counseling, information on the state of the counseling, and information on the duration of the counseling.

Figure 6A:
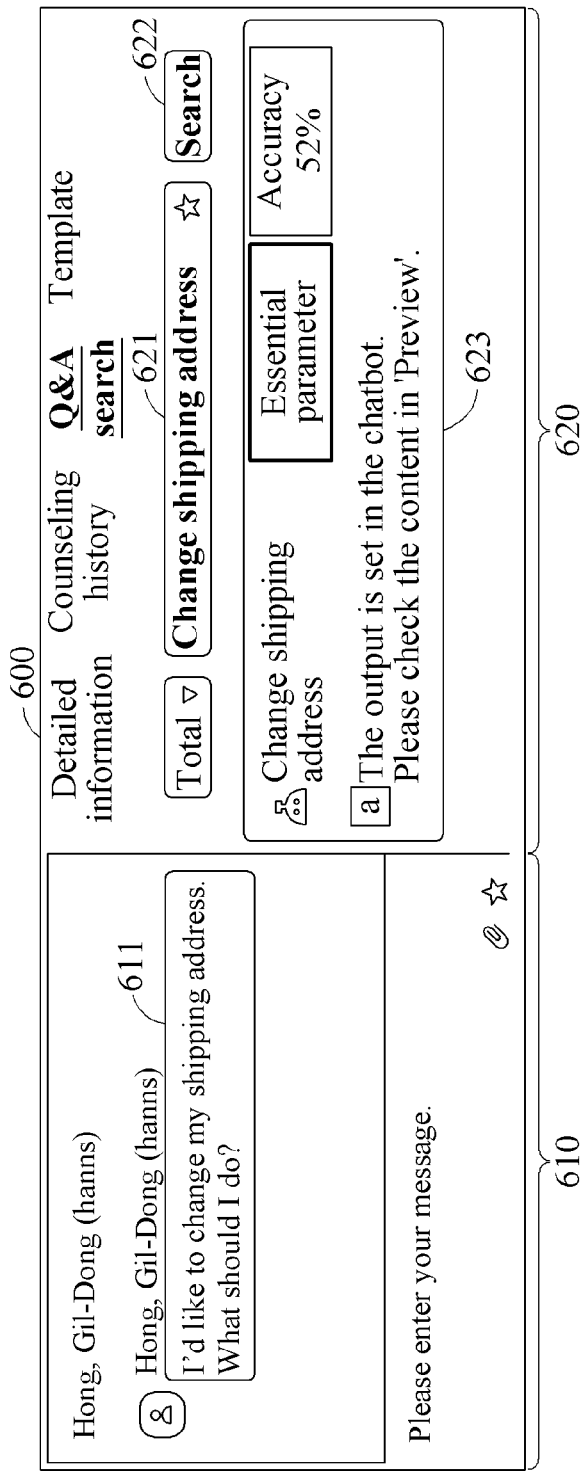
FIGS. 6A and 6B are diagrams illustrating a screen of an interface related to a counseling center module supporting a search function according to an example embodiment.
Figure 6B:
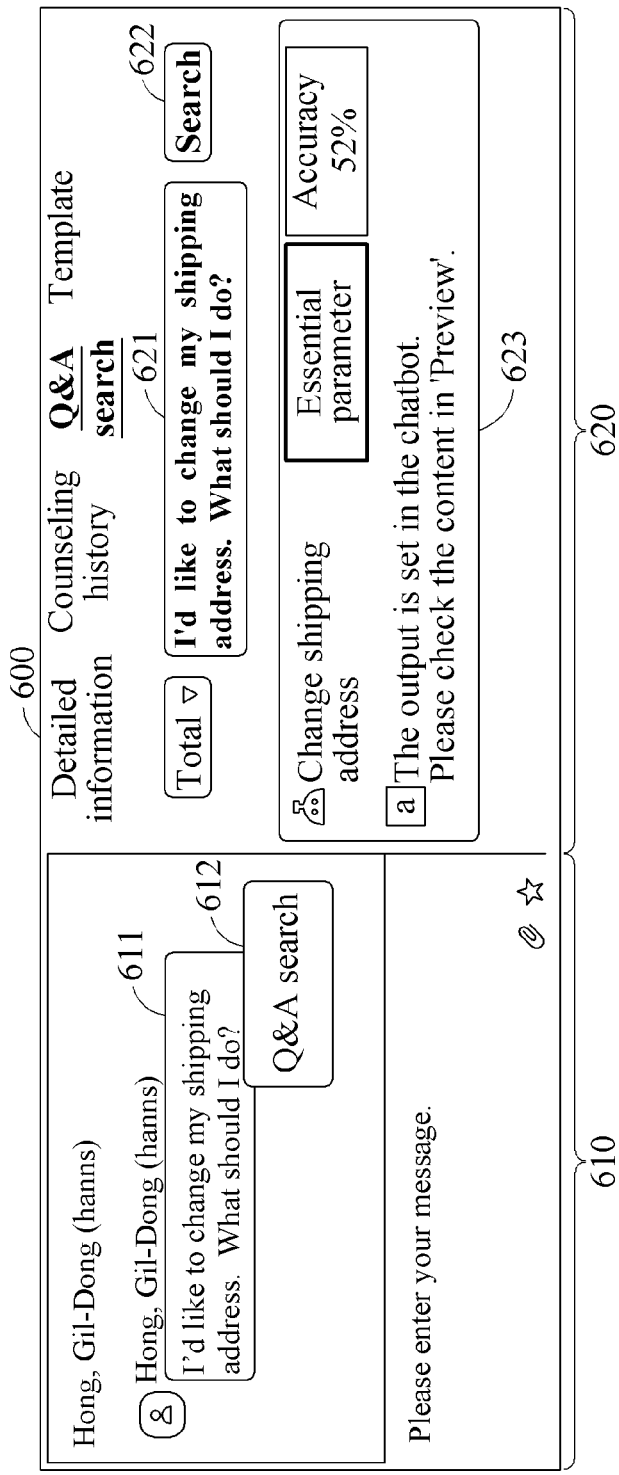

FIGS. 6A and 6B are diagrams illustrating a screen of an interface related to the counseling center module supporting a search function according to an example embodiment.

As described above, the counselor linked to a specific channel may be connected to the chat room of the channel created for the counseling through the interface related to the counseling center module provided in the terminal to conduct the counseling in a chatting manner with the user account requesting the counseling, and use the search function to call the chatbot block related to progress of the counseling.

Referring to FIGS. 6A and 6B, the interface 600 related to the counseling center module provided to the terminal of the counselor may transmit a search request to the chat window 610 corresponding to the chat room and the server, and include a search interface 620 for a search function for receiving the search result. A message 611 transmitted to the chat room for counseling may be displayed through the chat window 610, and the counselor may request the server to search for a specific search word based on the message 611 through the search window 621 included in the search interface 620.

For example, referring to FIG. 6A, based on a message 611 (e.g., "I'd like to change the shipping address. What should I do?") requesting the counseling regarding the change of the shipping address received by the counselor through the chat room, a search word (e.g., "change shipping address") may be directly input in the search window 621. As another example, referring to FIG. 6B, the chat window 610 may provide a function of transmitting a search request for the entire message to the server by an input (e.g., click) for selecting the interfacing object 612 requesting a search for the message 611. In response to the input of the counselor selecting the 'search' button 622, the terminal of the counselor may transmit a signal for requesting a search for the input search word to the server.

As described above, the server receiving the search request may transmit a query corresponding to the search request to the chatbot server linked to the counseling center module, and acquire a search result 623 corresponding to the search request received from the chatbot server. The chatbot server may identify a task corresponding to the input search request, and may provide information for calling a chatbot block corresponding to the identified task to the server as a search result. The chatbot block may be called through the chat room by an input (e.g., click) for selecting the search result 623 received from the terminal of the counselor.

Figure 7:
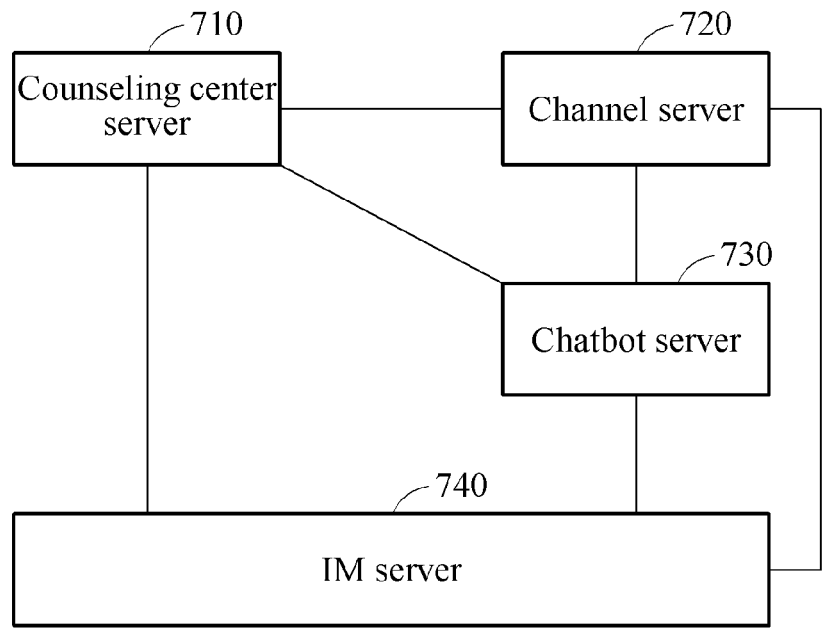
FIG. 7 is an exemplary diagram illustrating a configuration of a counseling system according to an example embodiment.

FIG. 7 is an exemplary diagram of a configuration of a counseling system according to an example embodiment.

Referring to FIG. 7, the counseling system according to an example embodiment may include a counseling center server 710, a channel server 720, a chatbot server 730, and an instant messaging server 740 (hereinafter, referred to as IM server).

The counseling system may perform an operation related to the counseling service conducted in a chatting manner between a personal account of a first user corresponding to a general user and a channel of a second user corresponding to a specific company or a specific service provider. The counselor linked to the channel of the second user may communicate with the counseling center server 710 through a counseling center app installed in the terminal of the counselor or a counseling center web accessed from the terminal of the counselor, and may transmit and receive messages through the chat room by accessing the chat room of the channel of the second user. The first user may communicate with the IM server 740 through the instant messaging app installed in the terminal of the first user or the instant messaging web accessed from the terminal, and may transmit and receive messages through the chat room by accessing the chat room of the channel of the second user.

According to an example embodiment, the terminal of the first user connected to the chat room of the channel of the second user may transmit a message to the chatbot server 730 or may transmit a message to the counselor linked to the channel of the second user. The recipient of the message may be determined depending on the type of counseling conducted in the chat room. For example, when the type of counseling conducted in the chat room of the channel of the second user is the unmanned counseling, a recipient of the message may be determined as the chatbot server 730 linked with the channel of the second user. When the type of counseling conducted in the chat room of the channel of the second user is the manned counseling, the recipient of the message may be determined as the counselor linked to the channel of the second user.

According to an example embodiment, the message transmitted from the terminal of the first user through the chat room of the channel may be transmitted to the IM server 740, and the IM server 740 may transmit the same to the counseling center server 710 or the chatbot server 730. For example, the IM server 740 may transmit the message to the counseling center server 710 when the message is transmitted to the counselor, and may transmit the message to the chatbot server 730 when the message is transmitted to the chatbot. The message transmitted to the chatbot server 730 may be transmitted from the chatbot server 730 to the counseling center server 710. The chatbot server 730 may create a response message for the message, and transmit the created response message to the terminal of the user through the IM server 740.

According to an example embodiment, the message transmitted from the terminal of the first user through the chat room of the channel is transmitted to the IM server 740, and the IM server 740 may transmit the same to the channel server 720 so that the channel server 720 may transmit to the counseling center server 710 or the chatbot server 730. The channel server 720 may process branching of a path through which the message is transmitted. In the case of a message transmitted to the counselor, the message may be transmitted to the counseling center server 710. In the case of a message transmitted to the chatbot, the message may be transmitted to the chatbot server 730.

According to an example embodiment, when the counseling ticket corresponding to the chat room of the channel through which the message is transmitted is not created, the counseling center server 710 may create the counseling ticket corresponding to the chat room. As described above, the type of the counseling ticket may be determined based on the type of counseling conducted in the chat room to which the message is transmitted. For example, when the counseling type at the time the message is transmitted is the unmanned counseling, the type of counseling ticket corresponding to the unmanned counseling may be created. When the counseling type at the time the message is transmitted is the manned counseling, the type of counseling ticket corresponding to the manned counseling may be created. According to an example embodiment, while a message is transmitted from the chatbot server 730 to the counseling center server 710, it is possible to request the counseling center server 710 to create the counseling ticket. The counseling center server 710 receiving the request for creating the counseling ticket from the chatbot server 730 may create a counseling ticket of a type corresponding to the unmanned counseling.

The counseling center server 710 may allocate the counseling ticket of a type corresponding to the manned counseling created in correspondence to the chat room of the channel of the second user to any one of accounts of counselors linked to the channel of the second user. The counseling center server 710 may transmit a message received through the chat room corresponding to the second type of counseling ticket to the terminal of the counselor to which the counseling ticket is allocated. The terminal of the counselor may request to transmit a message through the chat room corresponding to the counseling ticket allocated to the counseling center server 710, and the counseling center server 710 may transmit the message to the terminal of the user connected to the chat room through the IM server 740.

According to an example embodiment, the counseling center server may correspond to an electronic device including a processor, a memory, and an input/output device. The processor of the counseling center server according to an example embodiment may perform at least one operation described above with reference to FIGS. 1 and/or 4. For example, the processor may perform operations of the counseling center server interworking with the instant messaging service described above with reference to FIG. 1 and/or operations of the counseling center server interworking with the instant messaging service described above with reference to FIG. 4. In addition, the interface described above with reference to FIGS. 5 to 6B may be provided to the terminal of the counselor.

The memory of the counseling center server according to an example embodiment may be a computer-readable recording medium, and may be a volatile memory or a non-volatile memory. The memory according to an example embodiment may store information related to the provision of the counseling service described above with reference to FIGS. 1 and/or 4. For example, the memory of the server may store accounts of users registered in the server, and store the counseling center module created in correspondence to a channel registered in the server.

According to an example embodiment, the memory of the counseling center server may store a program in which at least one operation described above with reference to FIGS. 1 and/or 4 is implemented. The processor of the counseling center server may execute a program stored in the memory and control the server. The code of the program executed by the processor of the counseling center server may be stored in the memory.

The example embodiments described herein may be implemented using hardware components, software components, and/or a combination thereof. For example, the apparatus, method, and components described in the example embodiments may be implemented using a general purpose computer or special purpose computer, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may run an operating system (OS) and one or more software applications that run on the OS. The processing device may also access, store, manipulate, process, and create data in response to execution of the software. For purpose of simplicity, the description of a processing device is used as singular, however, one skilled in the art will appreciate that the processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct or configure the processing device to operate as desired. Software and/or data may be embodied permanently or temporarily in any type of machine, component, physical or virtual equipment, computer storage medium or device, or in a propagated signal wave capable of providing instructions or data to or being interpreted by the processing device. The software may also be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations which may be performed by a computer. The media may also include, alone or in combination with the program instructions, data files, data structures, and the like. The program instructions recorded on the media may be those specially designed and constructed for the purposes of the example embodiments, or they may be of the well-known kind and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as code produced by a compiler, and files containing higher level code that may be executed by the computer using an interpreter.

The described hardware devices may be configured to act as one or more software modules in order to perform the operations of the above-described example embodiments, or vice versa.

While this disclosure includes example embodiments, it will be apparent to one of ordinary skill in the art that various changes in form and details may be made in these example embodiments without departing from the spirit and scope of the claims and their equivalents. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A method of operating a user-assistance center server interworking with an instant messaging service, the method comprising:
    generating a user-assistance session by:
        establishing, via an instant messaging server, a communication session between a first terminal of a first user and a second terminal of a second user;
        causing display, at the first terminal of the first user, of a chat room interface that comprises a text input field;
        receiving, from the first user and via the text input field, a first user message; and
        causing display, at the second terminal of the second user, of the first user message;
    identifying a task corresponding to the first user message by comparing one or more first words of the first user message to one or more expected utterances associated with the task; and
    based on identifying the task, executing a chatbot mode by:
        activating a connection with a chatbot server;
        receiving, from the chatbot server, a plurality of different candidate output responses corresponding to the task;
        causing display, at the second terminal of the second user, of a user interface indicating a plurality of options that each correspond to a different candidate output response of the plurality of different candidate output responses, wherein each of the plurality of options indicates an accuracy parameter for a corresponding candidate output response;
        receiving, from the second terminal of the second user, a selection of a first option, of the plurality of options, that corresponds to a first output response of the plurality of different candidate output responses; and
        causing display, in the chat room interface displayed by the first terminal of the first user, of the first output response corresponding to the task.

2. The method of claim 1,
    receiving, from the first user, via the text input field, and after causing display of the first output response, a second user message; and
    causing display, at the second terminal of the second user, of the second user message.

3. The method of claim 1, wherein at least one of the plurality of different candidate output responses comprises a search result from the chatbot server.

4. The method of claim 1, further comprising:
    storing an association between the task and the one or more expected utterances, one or more actions, and one or more response messages.

5. The method of claim 1, wherein the activating the chatbot mode comprises:
    causing display, in the chat room interface, of an indication that the chatbot mode has been activated.

6. The method of claim 1, further comprising:
    based on user input requesting termination of the execution of the chatbot mode, terminating the execution of the chatbot mode.

7. The method of claim 1, further comprising:
    storing the first user message in a user-assistance ticket corresponding to the user-assistance session.

8. The method of claim 1, further comprising:
    causing display, at the first terminal of the first user, of a second user message received from the second terminal of the second user,
    wherein the second user message is visually distinguished from the first output response.

9. The method of claim 1, wherein the activating the connection with the chatbot server comprises transmitting, based on the execution of the chatbot mode, a message.

10. The method of claim 1, wherein the activating the connection with the chatbot server comprises executing, based on a request to execute the chatbot mode received from the second terminal of the second user, the chatbot mode.

11. A user-assistance center server interworking with an instant messaging service, wherein the user-assistance center server comprises:
    one or more processors; and
    memory storing instructions that, when executed by the one or more processors, cause the user-assistance center server to:
        generate a user-assistance session by:
            establishing, via an instant messaging server, a communication session between a first terminal of a first user and a second terminal of a second user;
            causing display, at the first terminal of the first user of a chat room interface that comprises a text input field;
            receiving, from the first user and via the text input field, a first user message; and
            causing display, at the second terminal of the second user, of the first user message;
        identify a task corresponding to the first user message by comparing one or more first words of the first user message to one or more expected utterances associated with the task; and
        based on identifying the task, execute a chatbot mode by:
            activating a connection with a chatbot server;
            receiving, from the chatbot server, a plurality of different candidate output responses corresponding to the task;
            causing display, at the second terminal of the second user, of a user interface indicating a plurality of options that each correspond to a different candidate output response of the plurality of different candidate output responses, wherein each of the plurality of options indicates an accuracy parameter for a corresponding candidate output response;
            receiving, from the second terminal of the second user, a selection of a first option, of the plurality of options, that corresponds to a first output response of the plurality of different candidate output responses; and causing display, in the chat room interface displayed by the first terminal of the first user, of the first output response corresponding to the task.

12. The user-assistance center server of claim 11, wherein the instructions, when executed by the one or more processors, further cause the user-assistance center server to:
receive, from the first user, via the text input field, and after causing display of the first output response, a second user message; and
cause display, at the second terminal of the second user, of the second user message.

13. The user-assistance center server of claim 11, wherein at least one of the plurality of different candidate output responses comprises a search result from the chatbot server.

14. The user-assistance center server of claim 11, wherein the instructions, when executed by the one or more processors, further cause the user-assistance center server to:
store an association between the task and the one or more expected utterances, one or more actions, and one or more response messages.

15. The user-assistance center server of claim 11, wherein the instructions, when executed by the one or more processors, cause the user-assistance center server to activate the chatbot mode by causing the user-assistance center server to:
cause display, in the chat room interface, of an indication that the chatbot mode has been activated.

16. One or more non-transitory computer-readable media storing instructions that, when executed by one or more processors of a user-assistance center server interworking with an instant messaging service, cause the user-assistance center server to:
generate a user-assistance session by:
establishing, via an instant messaging server, a communication session between a first terminal of a first user and a second terminal of a second user;
causing display, at the first terminal of the first user, of a chat room interface that comprises a text input field;
receiving, from the first user and via the text input field, a first user message; and
causing display, at the second terminal of the second user, of the first user message;
identify a task corresponding to the first user message by comparing one or more first words of the first user message to one or more expected utterances associated with the task; and
based on identifying the task, execute a chatbot mode by:
activating a connection with a chatbot server;
receiving, from the chatbot server, a plurality of different candidate output responses corresponding to the task;
causing display, at the second terminal of the second user, of a user interface indicating a plurality of options that each correspond to a different candidate output response of the plurality of different candidate output responses, wherein each of the plurality of options indicates an accuracy parameter for a corresponding candidate output response;
receiving, from the second terminal of the second user, a selection of a first option, of the plurality of options, that corresponds to a first output response of the plurality of different candidate output responses; and
causing display, in the chat room interface displayed by the first terminal of the first user, of the first output response corresponding to the task.

17. The one or more non-transitory computer-readable media of claim 16, wherein the instructions, when executed by the one or more processors, further cause the user-assistance center server to:
receive, from the first user, via the text input field, and after causing display of the first output response, a second user message; and
cause display, at the second terminal of the second user, of the second user message.

18. The one or more non-transitory computer-readable media of claim 16, wherein at least one of the plurality of different candidate output responses comprises a search result from the chatbot server.

19. The one or more non-transitory computer-readable media of claim 16, wherein the instructions, when executed by the one or more processors, further cause the user-assistance center server to:
store an association between the task and the one or more expected utterances, one or more actions, and one or more response messages.

20. The one or more non-transitory computer-readable media of claim 16, wherein the instructions, when executed by the one or more processors, cause the user-assistance center server to activate the chatbot mode by causing the user-assistance center server to:
cause display, in the chat room interface, of an indication that the chatbot mode has been activated.

* * * * *